(12) United States Patent
Twomey et al.

(10) Patent No.: US 11,490,954 B2
(45) Date of Patent: *Nov. 8, 2022

(54) GAP CONTROL VIA OVERMOLD TEETH AND HARD STOPS

(71) Applicant: Covidien LP, Mansfield, MA (US)

(72) Inventors: John R. Twomey, Longmont, CO (US); Dylan R. Kingsley, Broomfield, CO (US); James D. Allen, IV, Broomfield, CO (US); Sean T. O'Neill, Los Gatos, CA (US); Jeffrey M. Roy, Boulder, CO (US)

(73) Assignee: Covidien LP, Mansfield, MA (US)

( * ) Notice: Subject to any disclaimer, the term of this patent is extended or adjusted under 35 U.S.C. 154(b) by 204 days.

This patent is subject to a terminal disclaimer.

(21) Appl. No.: 16/905,970

(22) Filed: Jun. 19, 2020

(65) Prior Publication Data
US 2020/0315695 A1    Oct. 8, 2020

Related U.S. Application Data

(63) Continuation of application No. 15/927,629, filed on Mar. 21, 2018, now Pat. No. 10,702,332, which is a
(Continued)

(51) Int. Cl.
*A61B 18/14*      (2006.01)
*B29C 45/14*     (2006.01)
(Continued)

(52) U.S. Cl.
CPC ...... *A61B 18/1445* (2013.01); *A61B 18/1442* (2013.01); *A61B 18/1482* (2013.01);
(Continued)

(58) Field of Classification Search
CPC ............ A61B 18/1442; A61B 18/1445; A61B 18/1482; A61B 2017/00526;
(Continued)

(56) References Cited

U.S. PATENT DOCUMENTS

D249,549 S    9/1978    Pike
D263,020 S    2/1982    Rau, III
(Continued)

FOREIGN PATENT DOCUMENTS

CN    201299462 Y    9/2009
CN    202313713 U    7/2012
(Continued)

OTHER PUBLICATIONS

McLellan et al. "Vessel Sealing for Hemostasis During Gynecologic Surgery" Sales/Product Literature 1999.
(Continued)

*Primary Examiner* — George Manuel
(74) *Attorney, Agent, or Firm* — Carter, DeLuca & Farrell LLP

(57) ABSTRACT

A forceps includes an end effector assembly having a stop and a plurality of overmold teeth within at least one jaw member. One (or both) of the jaw members is moveable relative to the other between a spaced-apart position and an approximated position for grasping tissue therebetween. One (or both) of the jaw members includes a stop molded within an insulative housing, and an insulator plate with the overmold teeth formed from plastic. The overmold teeth extend through openings within a sealing plate and protrude past the tissue sealing surface of the sealing plate. The stop primarily controls the gap distance between opposing jaw members by bearing most of an applied load and the overmold teeth assist in controlling the gap distance by bearing the remaining applied load.

17 Claims, 9 Drawing Sheets

Related U.S. Application Data continuation of application No. 15/296,118, filed on Oct. 18, 2016, now Pat. No. 9,931,159, which is a continuation of application No. 14/718,748, filed on May 21, 2015, now Pat. No. 9,468,490, which is a continuation of application No. 14/578,953, filed on Dec. 22, 2014, now Pat. No. 9,192,434, which is a continuation of application No. 13/835,004, filed on Mar. 15, 2013, now Pat. No. 8,939,975.

(60) Provisional application No. 61/672,347, filed on Jul. 17, 2012.

(51) Int. Cl.

| | | |
|---|---|---|
| A61B 18/00 | (2006.01) | |
| A61B 90/00 | (2016.01) | |
| A61B 17/00 | (2006.01) | |
| B29L 31/00 | (2006.01) | |
| A61B 17/29 | (2006.01) | |

(52) U.S. Cl.
CPC .......... *B29C 45/14336* (2013.01); *A61B 2017/00526* (2013.01); *A61B 2017/2926* (2013.01); *A61B 2018/0063* (2013.01); *A61B 2018/00083* (2013.01); *A61B 2018/00589* (2013.01); *A61B 2018/00595* (2013.01); *A61B 2018/145* (2013.01); *A61B 2018/1455* (2013.01); *A61B 2090/034* (2016.02); *B29L 2031/7546* (2013.01)

(58) Field of Classification Search
CPC .. A61B 2017/2926; A61B 2018/00083; A61B 2018/00589; A61B 2018/00595; A61B 2018/0063; A61B 2018/145; A61B 2018/1455; A61B 2090/034; B29C 45/14336; B29L 2031/7546

See application file for complete search history.

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| 5,700,261 A | 12/1997 | Brinkerhoff |
| H1745 H | 8/1998 | Paraschac |
| D402,028 S | 12/1998 | Grimm et al. |
| D408,018 S | 4/1999 | McNaughton |
| 5,891,142 A | 4/1999 | Eggers et al. |
| D416,089 S | 11/1999 | Barton et al. |
| 6,030,384 A | 2/2000 | Nezhat |
| 6,030,808 A | 2/2000 | Darnell, Jr. et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,648,883 B2 | 11/2003 | Francischelli et al. |
| 6,663,627 B2 | 12/2003 | Francischelli et al. |
| 6,723,092 B2 | 4/2004 | Brown et al. |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| 6,926,716 B2 | 8/2005 | Baker et al. |
| D509,297 S | 9/2005 | Wells |
| 7,029,470 B2 | 4/2006 | Francischelli et al. |
| D525,361 S | 7/2006 | Hushka |
| 7,083,619 B2 | 8/2006 | Truckai et al. |
| 7,090,673 B2 | 8/2006 | Dycus et al. |
| 7,094,235 B2 | 8/2006 | Francischelli |
| 7,101,371 B2 | 9/2006 | Dycus et al. |
| D531,311 S | 10/2006 | Guerra et al. |
| 7,131,971 B2 | 11/2006 | Dycus et al. |
| D533,274 S | 12/2006 | Visconti et al. |
| D533,942 S | 12/2006 | Kerr et al. |
| D535,027 S | 1/2007 | James et al. |
| 7,169,146 B2 | 1/2007 | Truckai et al. |
| D538,932 S | 3/2007 | Malik |
| 7,186,253 B2 | 3/2007 | Truckai et al. |
| 7,189,233 B2 | 3/2007 | Truckai et al. |
| D541,418 S | 4/2007 | Schechter et al. |
| D541,611 S | 5/2007 | Aglassinge |
| D541,938 S | 5/2007 | Kerr et al. |
| D545,432 S | 6/2007 | Watanabe |
| D547,154 S | 7/2007 | Lee |
| 7,250,048 B2 | 7/2007 | Francischelli et al. |
| 7,255,697 B2 | 8/2007 | Dycus et al. |
| D564,662 S | 3/2008 | Moses et al. |
| D567,943 S | 4/2008 | Moses et al. |
| 7,354,440 B2 | 4/2008 | Truckai et al. |
| 7,367,972 B2 | 5/2008 | Francischelli et al. |
| 7,381,209 B2 | 6/2008 | Truckai et al. |
| D575,395 S | 8/2008 | Hushka |
| D575,401 S | 8/2008 | Hixson et al. |
| D582,038 S | 12/2008 | Swoyer et al. |
| 7,632,269 B2 | 12/2009 | Truckai et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,731,717 B2 | 6/2010 | Odom et al. |
| 7,744,562 B2 | 6/2010 | Jahns et al. |
| D621,503 S | 8/2010 | Otten et al. |
| 7,776,036 B2 | 8/2010 | Schechter et al. |
| 7,794,461 B2 | 9/2010 | Eder et al. |
| 7,799,026 B2 | 9/2010 | Schechter et al. |
| 7,803,156 B2 | 9/2010 | Eder et al. |
| D627,462 S | 11/2010 | Kingsley |
| D628,289 S | 11/2010 | Romero |
| D628,290 S | 11/2010 | Romero |
| 7,824,399 B2 | 11/2010 | Francischelli et al. |
| D630,324 S | 1/2011 | Reschke |
| 7,955,331 B2 | 6/2011 | Truckai et al. |
| D649,249 S | 11/2011 | Guerra |
| D649,643 S | 11/2011 | Allen, IV et al. |
| D661,394 S | 6/2012 | Romero et al. |
| 8,535,312 B2 | 9/2013 | Horner |
| 8,679,140 B2 | 3/2014 | Butcher |
| RE44,834 E | 4/2014 | Dumbauld et al. |
| 8,747,434 B2 | 6/2014 | Larson et al. |
| 8,752,264 B2 | 6/2014 | Ackley et al. |
| 8,887,373 B2 | 11/2014 | Brandt et al. |
| 8,920,461 B2 | 12/2014 | Unger et al. |
| 8,939,975 B2 | 1/2015 | Twomey et al. |
| 8,961,513 B2 | 2/2015 | Allen, IV et al. |
| 8,961,514 B2 | 2/2015 | Garrison |
| 8,968,298 B2 | 3/2015 | Twomey |
| 8,968,311 B2 | 3/2015 | Allen, IV et al. |
| 8,968,313 B2 | 3/2015 | Larson |
| 8,968,360 B2 | 3/2015 | Garrison et al. |
| 9,011,435 B2 | 4/2015 | Brandt et al. |
| 9,011,436 B2 | 4/2015 | Garrison |
| 9,023,039 B2 | 5/2015 | Kerr |
| 9,034,009 B2 | 5/2015 | Twomey et al. |
| 9,039,691 B2 | 5/2015 | Moua et al. |
| 9,072,524 B2 | 7/2015 | Heard et al. |

(56) References Cited

U.S. PATENT DOCUMENTS

| | | |
|---|---|---|
| 9,113,882 B2 | 8/2015 | Twomey et al. |
| 9,113,889 B2 | 8/2015 | Reschke |
| 9,113,897 B2 | 8/2015 | Deborski et al. |
| 9,113,901 B2 | 8/2015 | Allen, IV et al. |
| 9,113,904 B2 | 8/2015 | Kerr et al. |
| 9,161,769 B2 | 10/2015 | Stoddard et al. |
| 9,161,812 B2 | 10/2015 | Kerr |
| 9,168,052 B2 | 10/2015 | Garrison et al. |
| 9,192,421 B2 | 11/2015 | Garrison |
| 9,192,432 B2 | 11/2015 | Larson et al. |
| 9,192,434 B2 | 11/2015 | Twomey et al. |
| 9,265,569 B2 | 2/2016 | Hart et al. |
| 9,265,573 B2 | 2/2016 | Kerr |
| 9,375,258 B2 | 6/2016 | Kendrick |
| 9,375,282 B2 | 6/2016 | Nau, Jr. et al. |
| 9,468,490 B2 | 10/2016 | Twomey et al. |
| 9,545,262 B2 | 1/2017 | Kerr et al. |
| 9,693,816 B2 | 7/2017 | Orszulak |
| 9,713,493 B2 | 7/2017 | Waaler et al. |
| 9,820,765 B2 | 11/2017 | Allen, IV et al. |
| 9,918,771 B2 | 3/2018 | Regadas |
| 9,931,159 B2 | 4/2018 | Twomey et al. |
| 10,702,332 B2 | 7/2020 | Twomey et al. |
| 2002/0188294 A1 | 12/2002 | Couture et al. |
| 2007/0106297 A1 | 5/2007 | Dumbauld et al. |
| 2007/0156139 A1 | 7/2007 | Schechter et al. |
| 2007/0270795 A1 | 11/2007 | Francischelli et al. |
| 2008/0147062 A1 | 6/2008 | Truckai et al. |
| 2008/0319442 A1 | 12/2008 | Unger et al. |
| 2009/0082767 A1 | 3/2009 | Unger et al. |
| 2010/0069903 A1 | 3/2010 | Allen, IV et al. |
| 2010/0076432 A1 | 3/2010 | Horner |
| 2010/0179540 A1 | 7/2010 | Marczyk et al. |
| 2010/0179545 A1 | 7/2010 | Twomey et al. |
| 2011/0004208 A1 | 1/2011 | Truckai et al. |
| 2011/0270245 A1 | 11/2011 | Horner et al. |
| 2011/0270251 A1 | 11/2011 | Horner et al. |
| 2012/0083786 A1 | 4/2012 | Artale et al. |
| 2013/0185922 A1 | 7/2013 | Twomey et al. |
| 2013/0190755 A1 | 7/2013 | Deborski |
| 2013/0197503 A1 | 8/2013 | Orszulak |
| 2013/0218199 A1 | 8/2013 | Kerr et al. |
| 2013/0219691 A1 | 8/2013 | Reschke |
| 2013/0226178 A1 | 8/2013 | Brandt et al. |
| 2013/0226226 A1 | 8/2013 | Garrison |
| 2013/0253489 A1 | 9/2013 | Nau, Jr. et al. |
| 2013/0255063 A1 | 10/2013 | Hart et al. |
| 2013/0274736 A1 | 10/2013 | Garrison |
| 2013/0289561 A1 | 10/2013 | Waaler et al. |
| 2013/0296848 A1* | 11/2013 | Allen, IV ........... A61B 18/1445 606/41 |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0325057 A1 | 12/2013 | Larson |
| 2013/0345706 A1 | 12/2013 | Garrison |
| 2014/0005663 A1 | 1/2014 | Heard et al. |
| 2014/0005666 A1 | 1/2014 | Moua et al. |
| 2014/0025052 A1 | 1/2014 | Nau, Jr. et al. |
| 2014/0025060 A1 | 1/2014 | Kerr |
| 2014/0025067 A1 | 1/2014 | Kerr et al. |
| 2014/0025070 A1 | 1/2014 | Kerr et al. |
| 2014/0031821 A1 | 1/2014 | Garrison |
| 2014/0031860 A1 | 1/2014 | Stoddard et al. |
| 2015/0112337 A1 | 4/2015 | Twomey et al. |

FOREIGN PATENT DOCUMENTS

| | | |
|---|---|---|
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 102004026179 B4 | 1/2009 |
| DE | 102008018406 B3 | 7/2009 |
| DE | 202012100833 U1 | 4/2012 |
| EP | 1159926 A2 | 3/2003 |
| EP | 1486177 A2 | 12/2004 |
| EP | 1769767 A1 | 4/2007 |
| EP | 1810625 A1 | 7/2007 |
| EP | 2174612 A1 | 4/2010 |
| EP | 2377480 A1 | 10/2011 |
| EP | 2382937 A1 | 11/2011 |
| EP | 2436330 A1 | 4/2012 |
| EP | 2974685 A1 | 1/2016 |
| JP | 61501068 A | 5/1986 |
| JP | H055106 A | 1/1993 |
| JP | H0540112 A | 2/1993 |
| JP | H06502328 A | 3/1994 |
| JP | H06121797 A | 5/1994 |
| JP | H06285078 A | 10/1994 |
| JP | H06343644 A | 12/1994 |
| JP | H06511401 A | 12/1994 |
| JP | H07265328 A | 10/1995 |
| JP | H0856955 A | 3/1996 |
| JP | H08252263 A | 10/1996 |
| JP | H08289895 A | 11/1996 |
| JP | H08317934 A | 12/1996 |
| JP | H08317936 A | 12/1996 |
| JP | H09538 A | 1/1997 |
| JP | H0910223 A | 1/1997 |
| JP | H09122138 A | 5/1997 |
| JP | H10195 A | 1/1998 |
| JP | H1024051 A | 1/1998 |
| JP | H10155798 A | 6/1998 |
| JP | H1147150 A | 2/1999 |
| JP | H1170124 A | 3/1999 |
| JP | H11169381 A | 6/1999 |
| JP | H11192238 A | 7/1999 |
| JP | H11244298 A | 9/1999 |
| JP | 2000102545 A | 4/2000 |
| JP | 2000342599 A | 12/2000 |
| JP | 2000350732 A | 12/2000 |
| JP | 2001008944 | 1/2001 |
| JP | 2001029356 | 2/2001 |
| JP | 2001128990 A | 5/2001 |
| JP | 2001190564 A | 7/2001 |
| JP | 2001003400 | 11/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2006015078 A | 1/2006 |
| JP | 2006501939 A | 1/2006 |
| JP | 2006095316 A | 4/2006 |
| JP | 2011125195 A | 6/2011 |
| JP | 6030945 B2 | 11/2016 |
| SU | 401367 A1 | 10/1973 |

(56) References Cited

FOREIGN PATENT DOCUMENTS

| WO | 0036986 | A1 | 6/2000 |
|---|---|---|---|
| WO | 0059392 | A1 | 10/2000 |
| WO | 0115614 | A1 | 3/2001 |
| WO | 0154604 | A1 | 8/2001 |
| WO | 0245589 | A2 | 6/2002 |
| WO | 2006021269 | A1 | 3/2006 |
| WO | 2005110264 | A2 | 4/2006 |
| WO | 2008040483 | A1 | 4/2008 |

OTHER PUBLICATIONS

European Search Report dated Dec. 9, 2015, corresponding to European Application No. 15181833.3; 9 pages.
E. David Crawford "Evaluation of a New Vessel Sealing Device in Urologic Cancer Surgery", 2000.
Extended European Search Report dated Oct. 11, 2013 for EP 13 17 6829.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 13/731,674, filed Dec. 31, 2012, Siebrecht.
Michael Choti, "Abdominoperineal Resection with the LigaSure Vessel Sealing System and LigaSure Atlas 20 cm Open Instrument" Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Caarbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al., "Comparison of Healing Process Following Ligation with Sutures and Bipolar Vessel Sealing" Surgical Technology International (2001).
"Electrosurgery: A Historical Overview" Innovations in Electrosurgery; Sales-Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford, "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al. "Extended Left Hemicolectomy Using the LigaSure Vessel Sealing System" Innovations That Work; Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work,Jun. 2002.
Heniford et al. "Initial Research and Clinical Results with an Electrothermal Bipolar Vessel Sealer" Oct. 1999.
Heniford et al "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al., "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females". Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room"; Sales/Product Literature 2001.
Bergdahl et al., "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al., "Sutureless Closed Hemorrhoidectomy: A New Technique" Annals of Surgery, vol. 234, No. 1, Jul. 2001, pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy"; Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford, "Use of a Novel Vessel Sealing Technology in Management of the Dorsal Venous Complex" Sales/Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Tissue"; MICCAI 2005; LNCS 3750 pp. 624-632, Dated: 2005.

(56) References Cited

OTHER PUBLICATIONS

McLellan et al., "Vessel Sealing for Hemostasis During Pelvic Surgery" Int'l Federation of Gynecology and Obstetrics FIGO World Congress 2000, Washington, DC.
Summons to attend oral proceedings issued in corresponding Appl. No.: EP 15181833.3 dated Dec. 13, 2019 (10 pages).

* cited by examiner

GAP CONTROL VIA OVERMOLD TEETH AND HARD STOPS

CROSS-REFERENCE TO RELATED APPLICATIONS

This application is a continuation of U.S. patent application Ser. No. 15/927,629, filed on Mar. 21, 2018, now U.S. Pat. No. 10,702,332, which is a continuation of U.S. patent application Ser. No. 15/296,118, filed on Oct. 18, 2016, now U.S. Pat. No. 9,931,159, which is a continuation of U.S. patent application Ser. No. 14/718,748, filed on May 21, 2015, now U.S. Pat. No. 9,468,490, which is a continuation of U.S. patent application Ser. No. 14/578,953, filed on Dec. 22, 2014, now U.S. Pat. No. 9,192,434, which is a continuation of U.S. patent application Ser. No. 13/835,004, filed on Mar. 15, 2013, now U.S. Pat. No. 8,939,975, which claims the benefit of the filing date of provisional U.S. Patent Application No. 61/672,347, filed on Jul. 17, 2012, the entire contents of each of which are incorporated herein by reference.

INTRODUCTION

The present disclosure relates to surgical instruments and, more particularly, to a surgical instrument for controlling gap distance between jaw members using hard stops and overmold teeth.

INTRODUCTION

Electrosurgical instruments, e.g., electrosurgical forceps, utilize both mechanical clamping action and electrical energy to effect hemostasis by heating tissue to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue.

One method of controlling the gap distance, uses one or more ceramic dots on one or both jaw members. The ceramic dots are deposited atop one or both jaw members. The ceramic dots may be vapor deposited onto sealing plates. The ceramic dots project from the tissue engaging surface of one or both jaw members and the ceramic dots form a corresponding series of nonconductive stop members for controlling the separation distance between opposing jaw members when closed about tissue. Most ceramics are stable at elevated temperatures and usually exhibit low thermal and electrical conductivities. In addition, ceramic materials have high melting points and are resistant to oxidation, corrosion, or other forms of degradation to which metals are usually more prone. However, ceramic dots add substantial cost to the manufacture of the jaw members.

SUMMARY

As used herein, the term "distal" refers to the portion that is being described which is further from a user, while the term "proximal" refers to the portion that is being described which is closer to a user.

In accordance with one aspect of the present disclosure, a forceps includes an end effector assembly having a stop and a plurality of overmold teeth within at least one jaw member. One (or both) of the jaw members may be moveable relative to the other between a spaced-apart position and an approximated position for grasping tissue therebetween. One (or both) of the jaw members includes a stop molded within an insulative housing, and an insulator plate with the overmold teeth formed from plastic. The overmold teeth extend through openings within a sealing plate and protrude past the tissue sealing surface of the sealing plate. The stop primarily controls the gap distance between opposing jaw members by bearing most of an applied load and the overmold teeth assist in controlling the gap distance by bearing the remaining applied load.

According to an aspect of the present disclosure, an end effector assembly includes a pair of opposing jaw members configured to primarily control a gap distance between opposing jaw members. At least one of the jaw members includes an insulative base including a hard stop. The hard stop is configured to primarily control a gap distance between the opposing jaw members. At least one of the jaw members also includes a support base coupled to the insulative housing and an insulative plate coupled to the support base and formed with a plurality of overmold teeth and a sealing plate mounted to the insulative plate. The sealing plate includes a plurality of openings formed therein. The plurality of overmold teeth extend through the corresponding plurality of openings on the sealing plate and are configured to assist in controlling the gap distance between opposing jaw members.

According to aspects of the present disclosure, the hard stop may be remotely disposed relative to the sealing plate.

According to other aspects of the present disclosure, the plurality of overmold teeth may be configured to contact the corresponding plurality of overmold teeth on the opposing jaw member. Alternatively, the plurality of overmold teeth may be configured to contact the sealing plate on the opposing jaw member. The plurality of overmold teeth may also be located along a blade slot defined in the seal plate to facilitate grasping of tissue during tissue division.

According to a further aspect of the present disclosure, the hard stop may be configured to primarily control the gap distance by bearing most of the applied load as the end effector assembly grasps tissue.

According to another aspect of the present disclosure, the hard stop may be engaged when jaw members flex under the applied load.

According to yet another aspect of the present disclosure, a method of forming a jaw member of an end effector includes the steps of forming a support base and forming an insulative plate with a plurality of overmold teeth. The method further includes the steps of forming a sealing plate with a plurality of openings and mounting the insulative base to the support base. The method further includes the step of mounting the sealing plate onto the insulative plate with the plurality of overmold teeth extending through the plurality of openings on the sealing plate. The method further includes the step of overmolding an insulative housing with a hard stop around the support base to form the jaw member. When the end effector is closed around tissue the hard stop is configured to bear the majority of an applied load and the overmold teeth bear a smaller remaining portion of the applied load The method may further include that the insulative plate may be formed by injection molding. The method may also include that the hard stop may be remotely disposed relative to the sealing plate.

According to another aspect of the present disclosure, an end effector assembly includes a pair of opposing jaw members. At least one of the jaw members includes an insulative housing including a hard stop formed from a plastic material. The hard stop may be configured to bear the majority of an applied load as the end effector assembly is closed around tissue. At least one of the jaw members further includes a support base coupled to the insulative housing and an insulative plate molded from the plastic material with a plurality of overmold teeth and a sealing plate mounted to the insulative plate. The sealing plate includes a plurality of openings formed therein. The plurality of overmold teeth extend through the corresponding plurality of openings on the sealing plate past a tissue sealing surface of the sealing plate. The plurality of overmold teeth may be configured to ensure that the opposing jaw members are an appropriate gap distance apart.

BRIEF DESCRIPTION OF THE DRAWINGS

Various embodiments of the present disclosure are described herein with reference to the drawings wherein.

DETAILED DESCRIPTION

Figure 1:
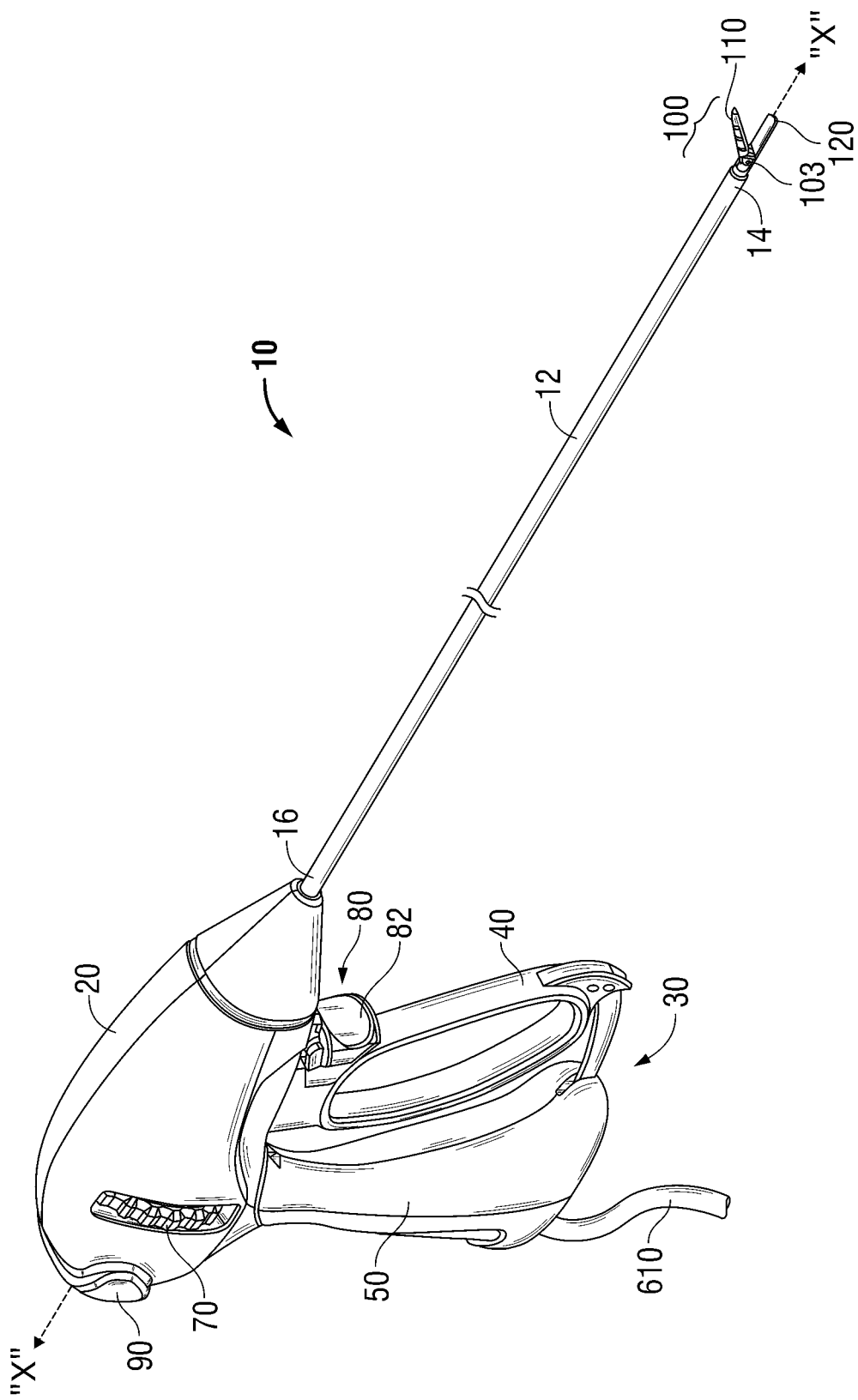
FIG. 1 is a front, perspective view of an endoscopic surgical instrument configured for use in accordance with the present disclosure.

Embodiments of the present disclosure are described in detail with reference to the drawing figures wherein like reference numerals identify similar or identical elements.

Figure 2:
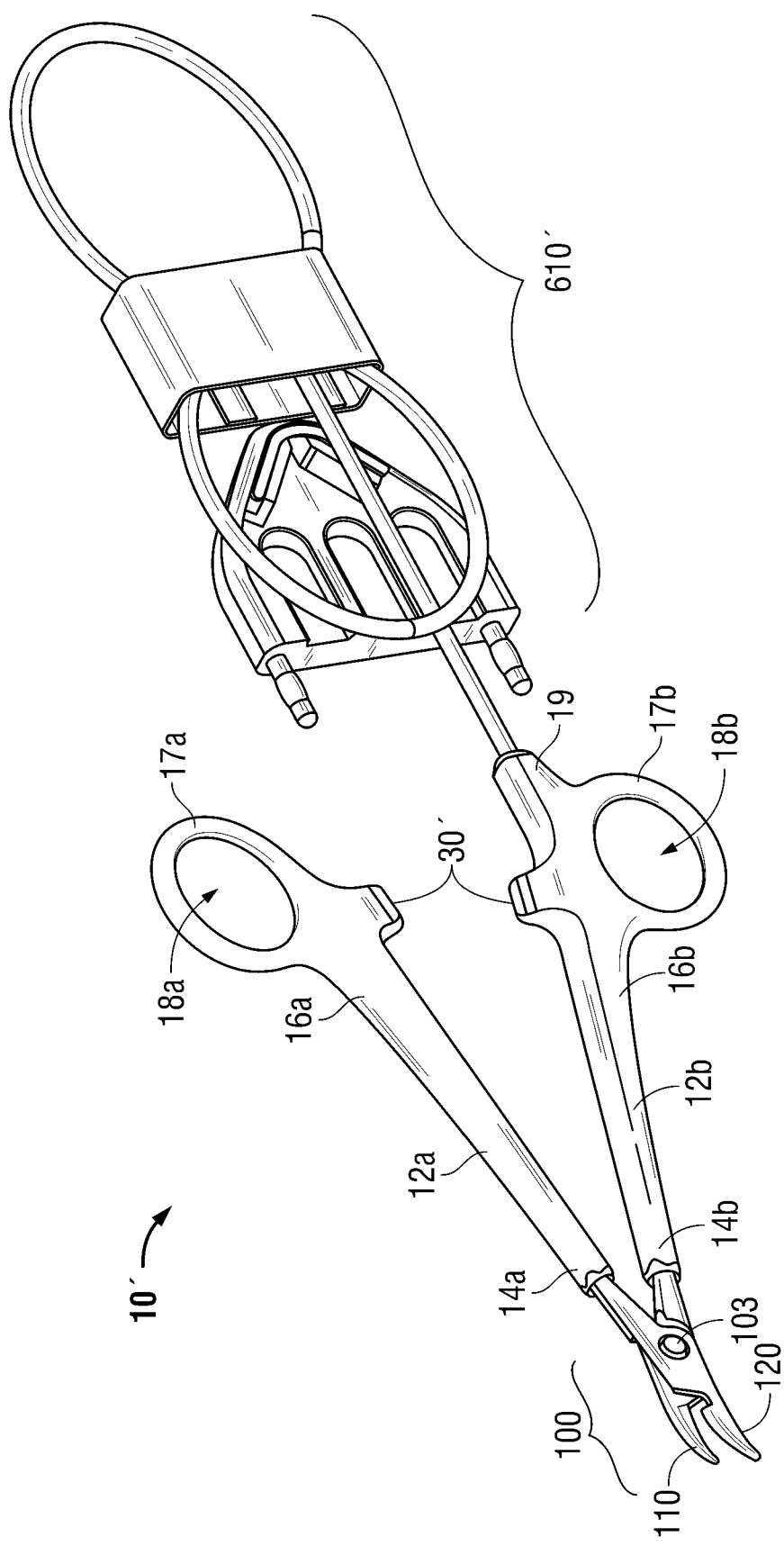
FIG. 2 is a front, perspective view of an open surgical instrument configured for use in accordance with the present disclosure.

Referring now to FIGS. 1 and 2, FIG. 1 depicts a forceps 10 for use in connection with endoscopic surgical procedures and FIG. 2 depicts an open forceps 10' contemplated for use in connection with traditional open surgical procedures. For the purposes herein, either an endoscopic instrument, e.g., forceps 10, or an open instrument, e.g., forceps 10', may be utilized in accordance with the present disclosure. Obviously, different electrical and mechanical connections and considerations apply to each particular type of instrument; however, the novel aspects with respect to the end effector assembly and the operating characteristics thereof remain generally consistent with respect to both the open and endoscopic configurations.

Turning now to FIG. 1, an endoscopic forceps 10 is provided defining a longitudinal axis "X-X" and including a housing 20, a handle assembly 30, a rotating assembly 70, a trigger assembly 80, an actuator 90, and an end effector assembly 100. Forceps 10 further includes a shaft 12 having a distal end 14 configured to mechanically engage end effector assembly 100 and a proximal end 16 that mechanically engages housing 20. Housing 20 contains the internal working components of the forceps 10 which are not described herein but which may be found in commonly-owned U.S. Pat. No. 7,156,846, the entire contents of which are hereby incorporated by reference herein.

End effector assembly 100 is shown attached at the distal end 14 of shaft 12 and includes a pair of opposing jaw members 110 and 120. Jaw members 110, 120 are moveable between a spaced-apart position and an approximated position for grasping tissue therebetween. End effector assembly 100 is designed as a unilateral assembly, e.g., where jaw member 120 is fixed relative to shaft 12 and jaw member 110 is moveable about pivot 103 relative to shaft 12 and fixed jaw member 120. However, end effector assembly 100 may alternatively be configured as a bilateral assembly, e.g., where both jaw member 110 and jaw member 120 are moveable about a pivot 103 relative to one another and to shaft 12.

With continued reference to FIG. 1, forceps 10 also includes electrosurgical cable 610 that connects forceps 10 to a generator (not shown) or other suitable power source, although forceps 10 may alternatively be configured as a battery powered instrument. Cable 610 includes a wire (or wires) (not explicitly shown) extending therethrough that has sufficient length to extend through shaft 12 in order to provide electrical energy to at least one of the jaw members 110 and 120 of end effector assembly 100. Trigger 82 of trigger assembly 80 may be selectively depressed to advance a knife (not shown) between jaw members 110, 120 to cut tissue grasped therebetween. Actuator 90, on the other hand, is selectively activatable to supply electrosurgical energy to one (or both) of jaw members 110, 120, as will be described in greater detail below.

With continued reference to FIG. 1, handle assembly 30 includes fixed handle 50 and a moveable handle 40. Fixed handle 50 is integrally associated with housing 20 and handle 40 is moveable relative to fixed handle 50. Rotating assembly 70 is rotatable in either direction about a longitudinal axis "X-X" to rotate end effector 100 about longitudinal axis "X-X." Moveable handle 40 of handle assembly 30 is ultimately connected to a drive assembly (not shown) that, together, mechanically cooperate to impart movement of jaw members 110 and 120 between the spaced-apart position and the approximated position to grasp tissue disposed between jaw members 110, 120. As shown in FIG. 1, moveable handle 40 is initially spaced-apart from fixed handle 50 and, correspondingly, jaw members 110, 120 are in the spaced-apart position. Moveable handle 40 is depressible from this initial position to a depressed position corresponding to the approximated position of jaw members 110, 120.

Referring now to FIG. 2, an open forceps 10' is shown including two elongated shafts 12a and 12b, each having a proximal end 16a and 16b, and a distal end 14a and 14b, respectively. Similar to forceps 10 (FIG. 1), forceps 10' is configured for use with end effector assembly 100. More specifically, end effector assembly 100 is attached to distal ends 14a and 14b of shafts 12a and 12b, respectively. As mentioned above, end effector assembly 100 includes a pair of opposing jaw members 110 and 120 that are pivotably connected about a pivot 103. Each shaft 12a and 12b includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of the shafts 12a and 12b relative to one another that, in turn, pivots jaw members 110 and 120 from an open position, wherein the jaw members 110 and 120 are disposed in spaced-apart relation relative to one another, to a closed position, wherein the jaw members 110 and 120 cooperate to grasp tissue therebetween.

A ratchet 30' may be included for selectively locking the jaw members 110 and 120 relative to one another at various positions during pivoting. Ratchet 30' may include graduations or other visual markings that enable the user to easily and quickly ascertain and control the amount of closure force desired between the jaw members 110 and 120.

With continued reference to FIG. 2, one of the shafts, e.g., shaft 12b, includes a proximal shaft connector 19 that is configured to connect the forceps 10' to a source of electrosurgical energy such as an electrosurgical generator (not shown). Proximal shaft connector 19 secures an electrosurgical cable 610' to forceps 10' such that the user may selectively apply electrosurgical energy to jaw member 110 and/or jaw member 120 of end effector assembly 100.

Figure 3:
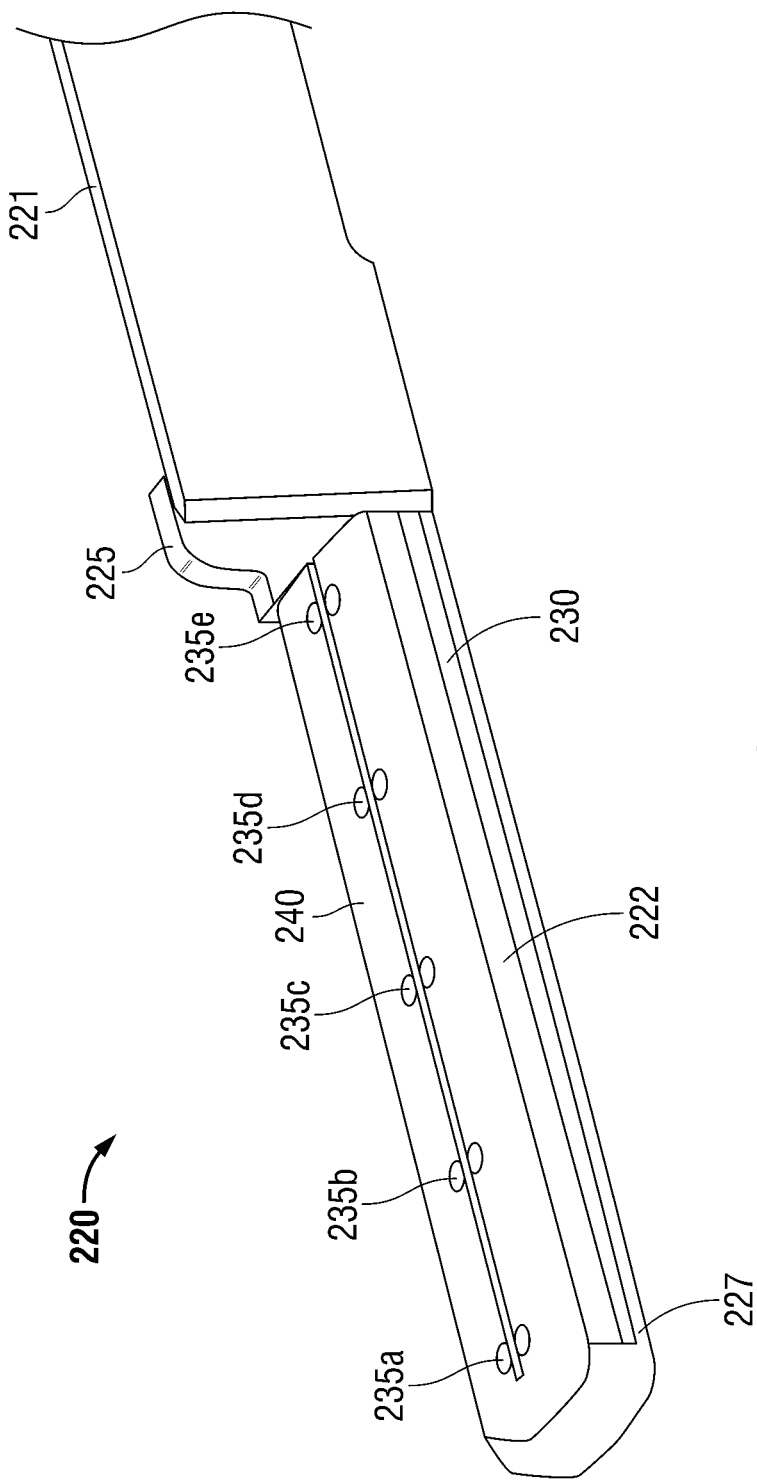
FIG. 3 is a front, perspective view of one embodiment of a jaw member configured for use with the surgical instrument of FIG. 1 or 2.
Figure 4:
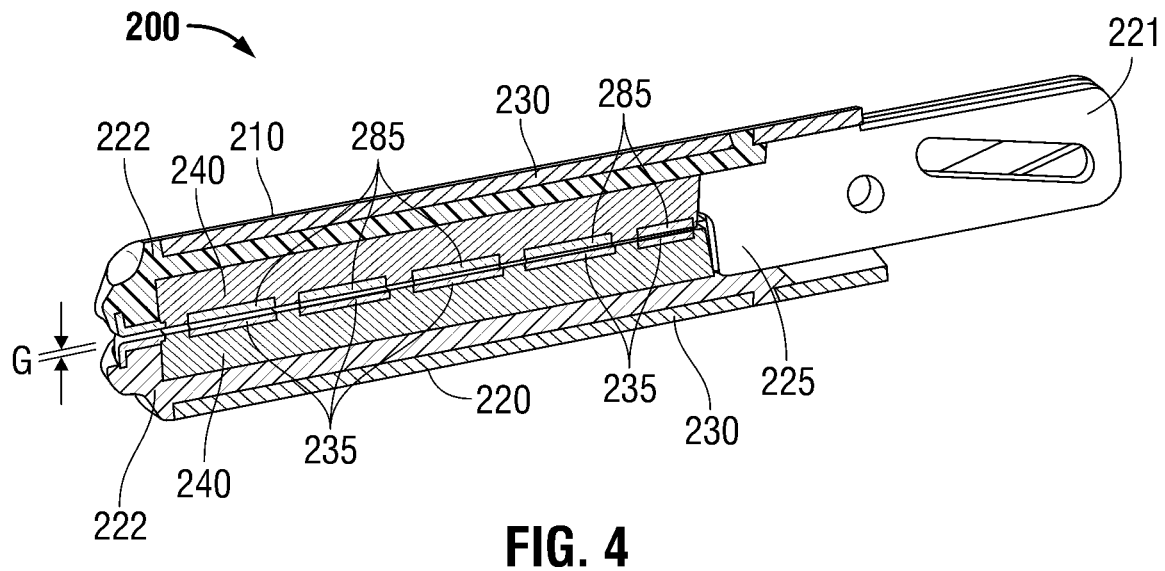
FIG. 4 is a side, perspective view of an end effector assembly configured for use with the surgical instrument of FIG. 1 or 2.
Figure 5:
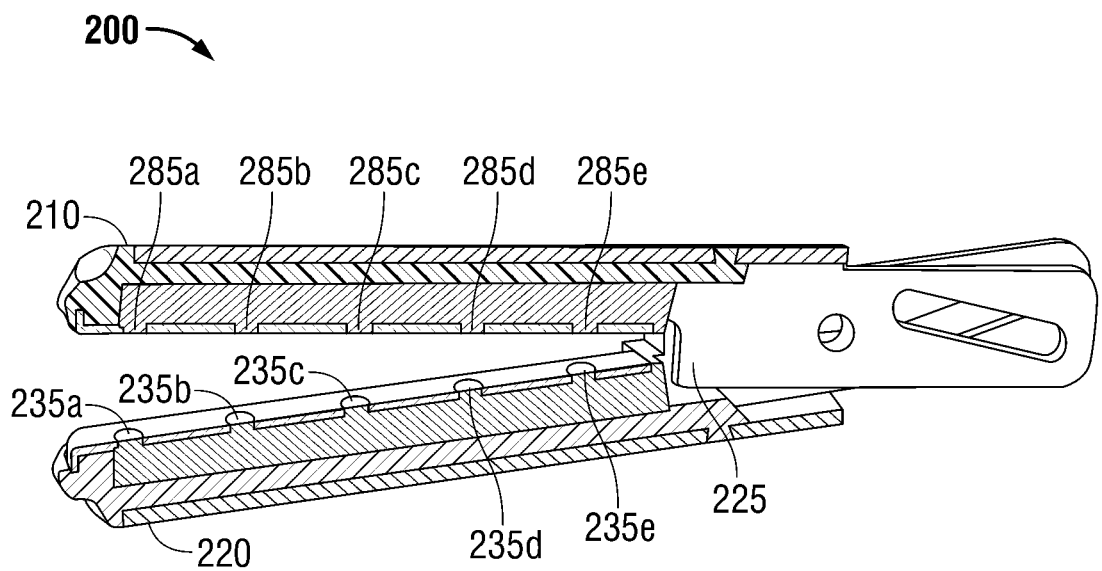
FIG. 5 is cross-sectional view of an end effector assembly configured for use with the surgical instrument of FIG. 1 or 2.

Referring now to FIGS. 3-5, one embodiment of jaw members 210 and 220 is provided in accordance with the present disclosure. FIG. 3 shows a front perspective view of jaw member 220. Jaw member 220 includes an insulative housing 227, support base 230, insulative plate 222, and sealing plate 240. Molded within the insulative housing 227 is a hard stop 225 configured to limit the gap distance when jaw members 220 and 210 (see FIG. 4) are closed around tissue. Additionally, overmold teeth 235a-235e assist in limiting the gap distance "G" (See FIG. 4) when jaw members 210 and 220 are closed around tissue.

One or more overmold teeth 235a-235e on jaw member 220 contact one or more respective opposing overmold teeth 285a-285e (see FIG. 4) on jaw member 210 as the jaw members 210, 220 are closed due to a tip-bias. Then as the jaw members 210, 220 flex one or more hard stops 225, and/or 275 are engaged. When the hard stops 225 and/or 275 are engaged, hard stops 225 and/or 275 bear most of the load. By having the one or more overmold teeth 235a-235e, 285a-285e contact first ensures that the jaw members are at the appropriate gap distance "G" (see FIG. 4). In other words, the tip-bias ensures that the jaw members 210, 220 are properly closing.

Alternatively, hard stop 225 and/or 275 may be configured to control the initial gap distance between jaw members 210 and 220 and to bear most of the load as the tissue is compressed between jaw members 210 and 220 while overmold teeth 235a-235e control the gap distance while jaw members 210 and 220 flex as they seal tissue.

As the jaw members 210, 220 clamp together around tissue, hard stop 225 and/or hard stop 275 (See FIG. 6A) and overmold teeth 235a-235e and/or 285a-285e maintain the gap distance "G" with the hard stop 225 and/or 275 bearing most of the applied load. The gap distance is about 0.001 inches to about 0.005 inches.

Hard stop 225 may be disposed at a remote location or away from the high temperatures of seal plate 240 (e.g., closer to proximal end 221 of jaw member 220) to reduce deflection of hard stop 225 under loading. By hard stops 225 and/or 275 being removed from the high temperatures of the seal plates 240, 312, the hard stops 225 and/or 275 can bear a majority of the applied load when a user grasps tissue with end effector 200 without the unnecessary risk of melting or deflection.

The overmold teeth 235a-235e and/or 285a-285e may be used to assist the user in gripping tissue during grasping. The overmold teeth 235a-235e and/or 285a-285e are relatively small in size to reduce the effect of the overmold teeth 235a-235e and/or 285a-285e on tissue sealing performance. For example the overmold teeth may range from about 0.020 inches to about 0.050 inches in diameter. However, the size of the teeth can vary based on the size of the jaw members. Initially, one or more overmold teeth 235a-235e and/or 285a-285e may be used to check that jaw members 210, 220 are closing to the gap distance "G". Then, as the jaw members 210, 220 flex then hard stops 225 and/or 275 make contact and bear most of the load. Alternatively, the overmold teeth 235a-235e and/or 285a-285e may be used to secondarily control the gap distance "G" as the jaw members 220, 210 flex. For example, when the jaw members flex 220, 210 under a particular loading condition, only one overmold tooth 235a may make contact with a corresponding opposing overmold tooth 285a. Alternatively, when the jaw members 220, 210 are under a different loading condition, more overmold teeth 235a-235e on jaw member 220 may make contact with corresponding overmold teeth 285a-285e on jaw member 210, however not all overmold teeth 235a-235e and/or 285a-285e need to contact each other to maintain proper gap distance "G".

Figure 6A:
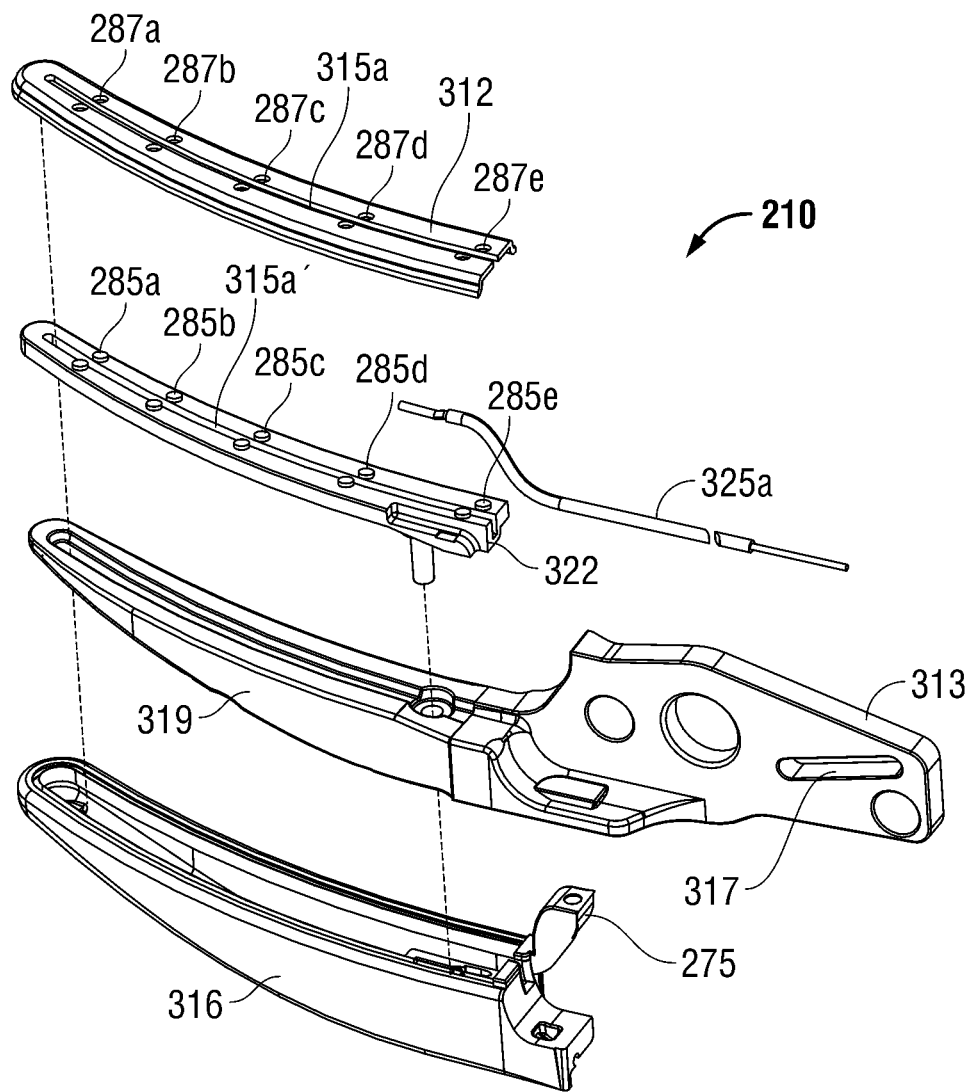
FIGS. 6A and 6B are exploded views of the opposing jaw members of FIG. 4.
Figure 6B:
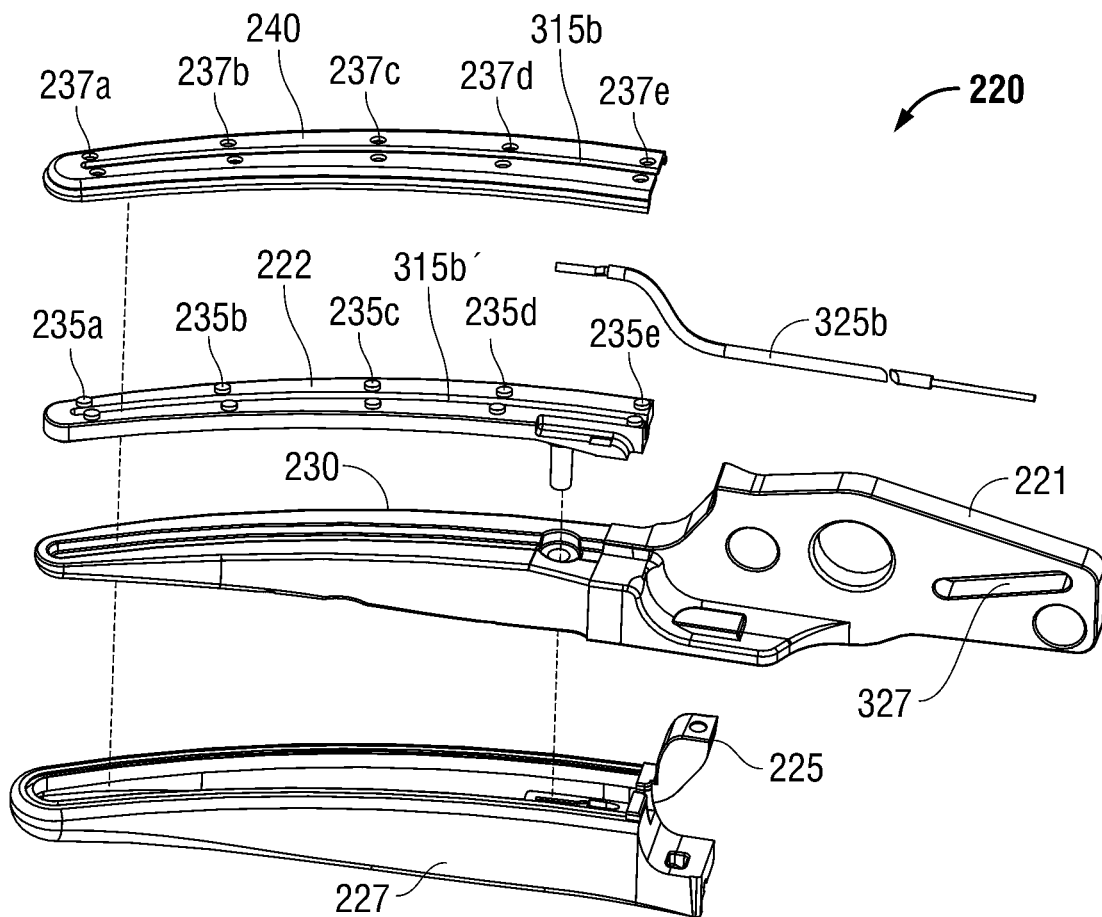

Turning to FIGS. 6A and 6B, the opposing jaw members 210 and 220 include support bases 319 and 230 that extend distally from flanges 313 and 221, respectively. The support bases 319 and 230 are configured to support insulative plates 322 and 222, which, in turn, support electrically conductive sealing plates 312 and 240 thereon. Sealing plates 312 and 240 may be affixed atop the insulative plates 322 and 222, respectively, and support bases 319 and 230, respectively, in any suitable manner including snap-fit, over-molding, stamping, ultrasonically welded, etc. The support bases 319 and 230, insulative plates 322 and 222, and sealing plates 312 and 240 are encapsulated by the outer insulative housings 316 and 227 by way of a subsequent overmolding process. The jaw members 210 and 220 are connected via an ultrasonic weld or other suitable joining process to electrical jaw leads 325a and 325b, respectively.

The jaw members 210 and 220 also include proximal flanges 313 and 221 extending proximally from the support bases 319 and 230, respectively, each of which includes an elongated angled cam slot 317 and 327, respectively, defined therethrough. The electrically conductive sealing plates 312 and 240 and the insulator plates 322 and 222 include respective longitudinally-oriented knife slots 315a, 315a' and 315b, 315b', respectively, defined therethrough for reciprocation of the knife blade (not shown). Jaw member 220 further includes one or more overmold teeth 235a-235e disposed on the inner facing surface of insulative plate 222 to define a gap between opposing jaw members 210 and 220 during sealing and/or cutting of tissue. The overmold teeth 235a-235e are molded within insulative plate 222 when the insulative plate 222 is molded. Types of plastic material that may be used are Amodel®, Trogamid®, PEKK, G-PEAK, PEEK, Thermotuff™, Ultem®, etc., all of which may be mineral and/or fiber reinforced.

The overmold teeth 235a-235e may be located along blade slot 315b'. The overmold teeth 235a-235e extend through openings 237a-237e within seal plate 240 and are slightly higher in elevation than seal plate 240 to prevent seal plates 312 and 240 from touching and creating a short between the seal plates 312, 240. Additionally, when the overmold teeth 235a-235e are located along blade slot 315b', the overmold teeth 235a-235e help grip tissue closer to where the division takes place and may produce a more reliable cut even when a blade (not shown) is not as sharp. Additionally, if insulator plate 322 includes one or more overmold teeth 285a-285e, then overmold teeth 285a-285e extend through openings 287a-287e within seal plate 312 and are slightly higher in elevation than seal plate 312 to prevent seal plates 312 and 240 from touching. Overmold teeth 285a-285e are formed in the same manner used to create overmold teeth 235a-235e. Additionally, if overmold teeth 285a-285e are spaced apart along blade slot 315a', then overmold teeth 285a-285e assist in gripping tissue closer to where the division takes place.

Figure 7A:
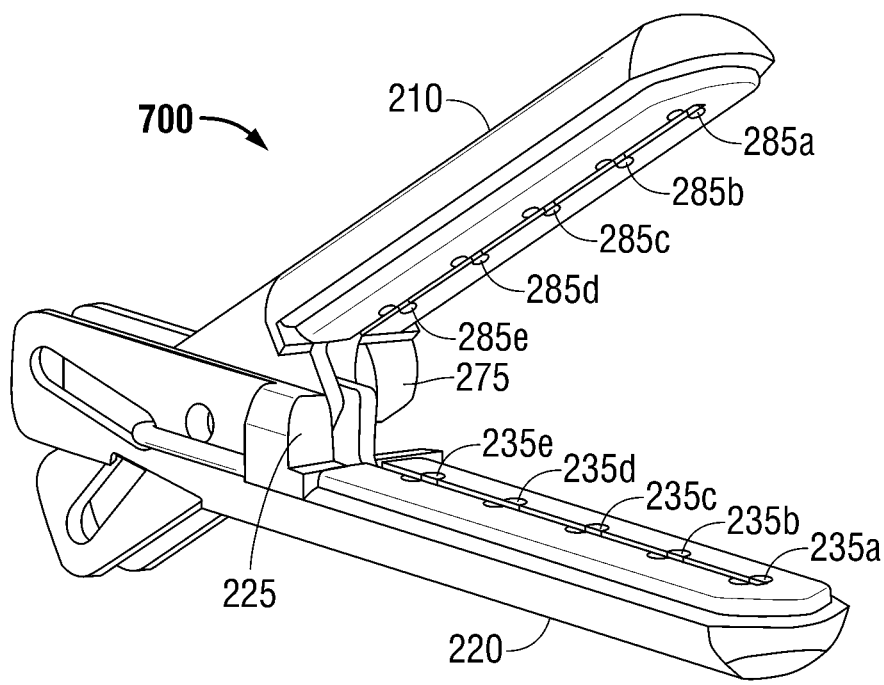
FIGS. 7A-7C are front, perspective views of different embodiments of an end effector assembly configured for use with the surgical instrument of FIG. 1 or 2.
Figure 7B:
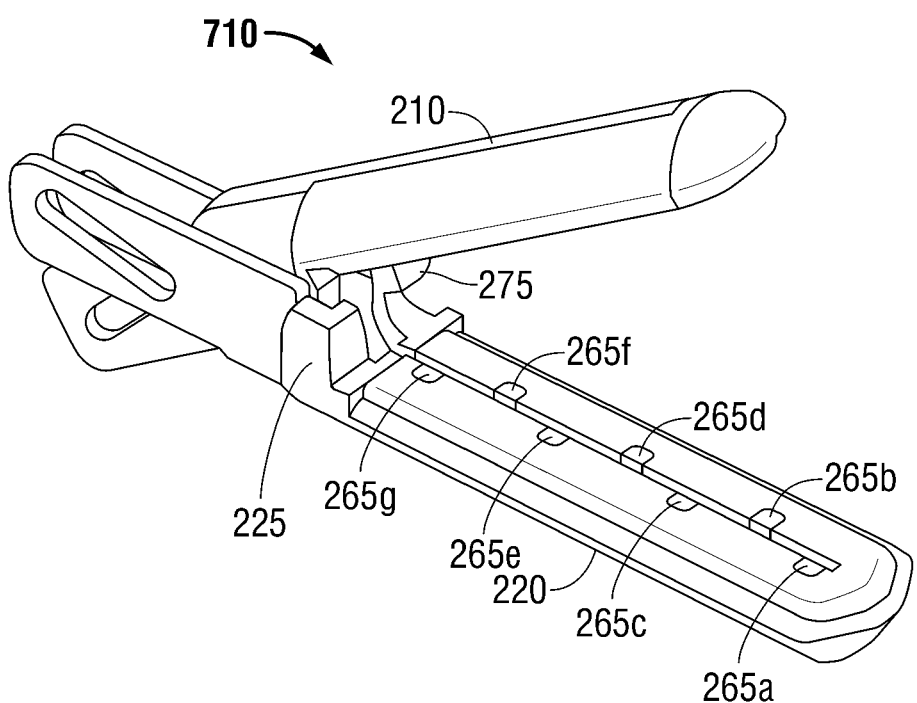
Figure 7C:
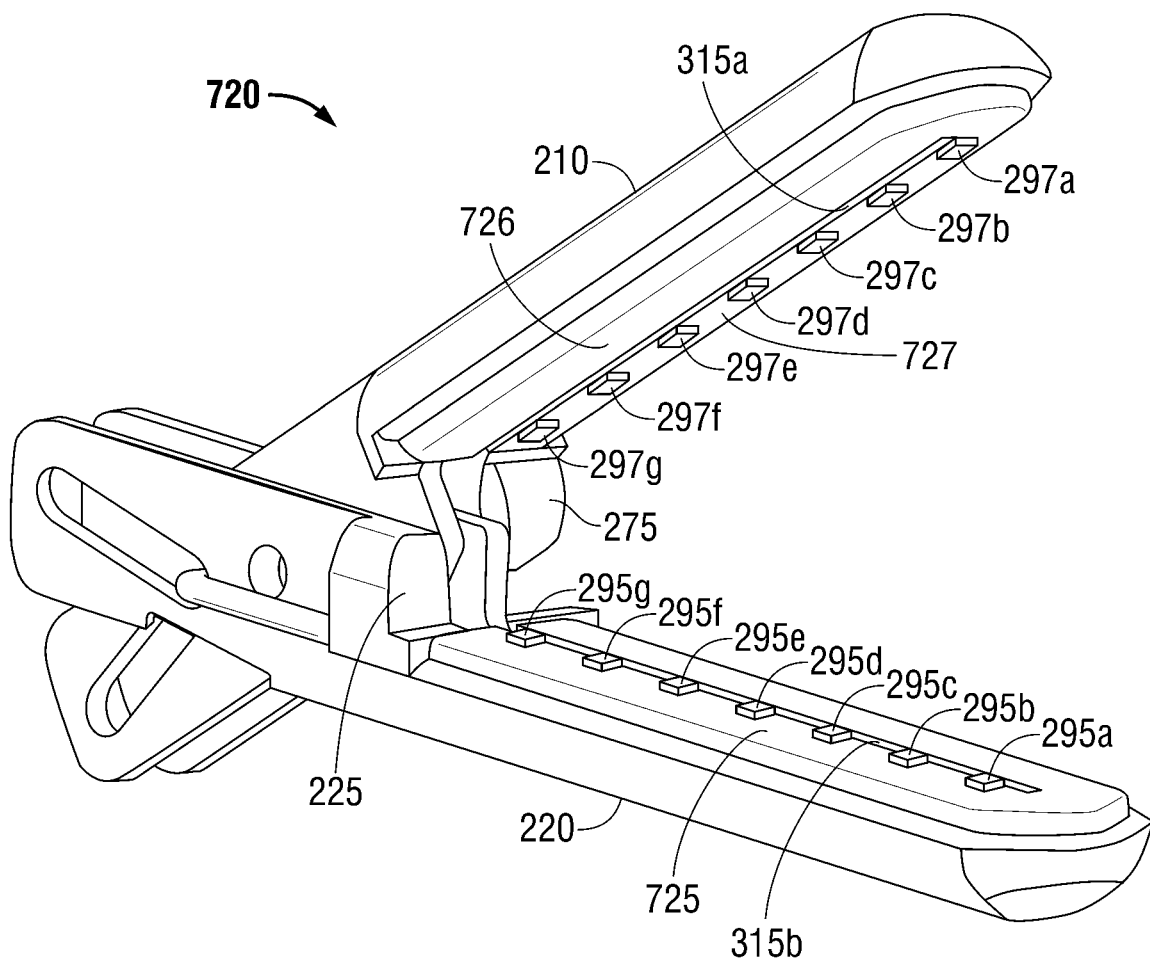

Referring to FIGS. 7A-7C, the overmold teeth 235a-235e and/or 285a-285e may be located in any location along insulative plates 222, 322 and either insulative plate 222 or 322 may include one or more overmold teeth 235a-235e and/or 285a-285e. FIG. 7A shows one embodiment of an end effector assembly 700 where the overmold teeth 235a-235e on jaw member 220 contact the mating row of overmold teeth 285a-285e on jaw member 210. With end effector 700, the overmold teeth 235a-235e and/or 285a-285e are almost always contacting plastic. FIG. 7B shows an alternative embodiment with end effector assembly 710, with overmold teeth 265a-265g on alternating sides blade slot 315b (See FIG. 6B). With end effector 710, each tooth of the overmold teeth 265a-265g may contact directly against seal plate 312 because of the symmetry with overmold teeth (not shown) on jaw member 210. However, if overmold teeth 265a-265g are of opposite symmetry to overmold teeth (not shown) on jaw member 210, then each tooth may contact an opposite overmold tooth, i.e. contact plastic and not a sealing plate 240, 312. Additionally, if only one jaw member 210 or 220 has overmold teeth 235a-235e or 285a-285e, then one or more teeth of the overmold teeth 235a-235e or 285a-285e contact the opposite seal plate 240, 312.

FIG. 7C shows an alternative end effector assembly 720. End effector assembly 720 includes a row of overmold teeth 295a-295g along a first side 725 of blade slot 315b on jaw member 220 and a row of overmold teeth 297a-297g along a second side 727 of blade slot 315a on jaw member 210. When end effector assembly 720 is closed around tissue, overmold teeth 295a-295g and 297a-297g contact directly against seal plate 312, 240 on respective opposing jaw members 210, 220. Alternatively, end effector 720 may be configured with a row of overmold teeth 295a-295g along a first side 725 of blade slot 315b on jaw member 220 and a row of overmold teeth 297a-297g along a first side 726 of blade slot 315a on jaw member 210. In this alternative embodiment, the overmold teeth 295a-295g and 297a-297g directly oppose each other and are almost always contacting plastic.

Figure 8:
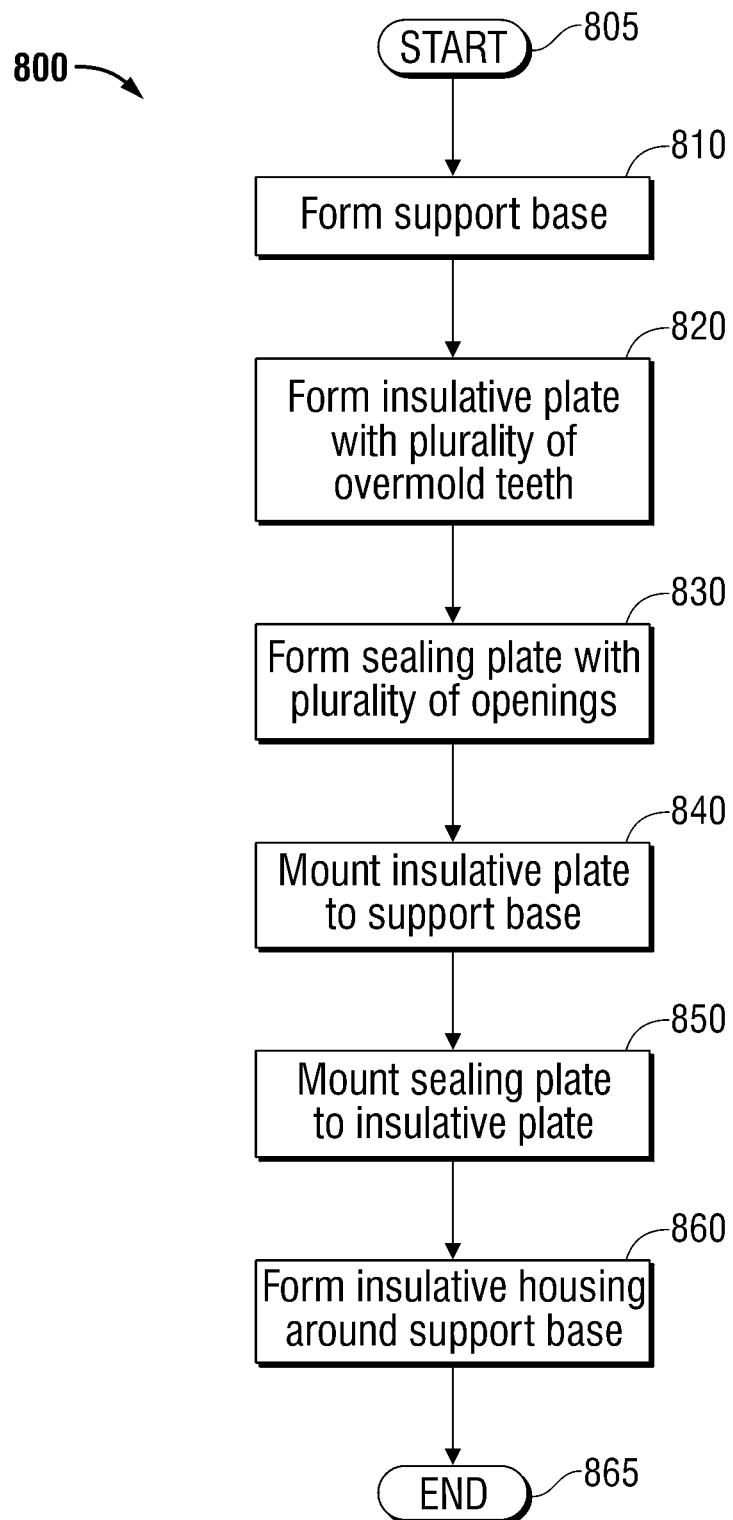
FIG. 8 is a flowchart of a method for forming a jaw member according to the present disclosure.

FIG. 8 is a flow diagram of process 800 for forming a jaw member 210, 220. The process 800 starts at step 805, and at step 810 the support base 230, 319 is formed. The support base 230, 319 may be formed of a plastic material by an injection molding process. Next, at step 820, an insulative plate 222, 322 with a plurality of overmold teeth 235a-235e, 285a-285e is formed of a plastic material by an injection molding process. Then at step 830, the sealing plate 240, 312 is formed from a conductive material with a plurality of openings 237a-237e, 287a-287e. Next at step 840, the insulative plate 222, 312 is mounted to the support base 230, 319. Then at step 850, the sealing plate 240, 312 is mounted to the insulative plate 222, 312 with the plurality overmold teeth 235a-235e, 285a-285e extending through the plurality of openings 237a-237e, 287a-287e, respectively. The sealing plate 240, 312 may be affixed atop the insulative plate 222, 312 in any known manner in the art, snap-fit, overmolding, stamping, ultrasonically welded, etc. The process 800 ends at step 865 after the insulative housing 227, 316 is formed around support base 230, 319 at step 860. When the insulative housing 227, 316 is formed hard stop 225, 275 is also formed of a plastic material. One method for forming the insulative housing 227, 316 is by an overmolding process.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps for use in a surgical procedure, the forceps comprising:
    a shaft having a proximal portion and a distal portion; and
    first and second jaw members disposed at the distal portion of the shaft, the first jaw member including:
        a sealing plate defining an opening therethrough;
        an overmold tooth extending through the opening and beyond the sealing plate towards the second jaw member; and
        a hard stop extending from the first jaw member beyond the sealing plate towards the second jaw member further than the overmold tooth, the hard stop configured to control a gap distance between the first and second jaw members.

2. The forceps according to claim 1, wherein the hard stop is disposed adjacent to an end of the sealing plate.

3. The forceps according to claim 1, wherein the sealing plate includes a longitudinally extending blade slot defined therein.

4. The forceps according to claim 1, wherein the first jaw member includes:
    a support base; and
    an insulative material disposed between the support base and the sealing plate.

5. The forceps according to claim 4, wherein the overmold tooth extends from the insulative material through the opening and beyond the sealing plate towards the second jaw member.

6. The forceps according to claim 4, further comprising an insulative housing mounted to the support base and encapsulating at least a portion of each of the support base, the insulative material, and the sealing plate.

7. A method of forming an end effector of a surgical forceps, comprising:
    assembling a sealing plate on a first jaw member, the sealing plate defining an opening therethrough;
    forming an overmold tooth extending through the opening beyond the sealing plate towards a second jaw member; and
    securing a hard stop relative to the sealing plate such that the hard stop extends beyond the sealing plate further than the overmold tooth and is configured to control a gap distance between the first and second jaw members.

8. The method according to claim 7, further comprising:
    assembling a support base with an insulative material and the sealing plate such that the insulative material is disposed between the support base and the sealing plate.

9. The method according to claim 7, further comprising mounting an insulative housing to the support base.

10. The method according to claim 9, wherein mounting the insulative housing the support base includes molding the insulative housing around at least a portion of the insulative material.

11. The method according to claim 9, wherein mounting the insulative housing the support base includes molding the insulative housing around a least a portion of the sealing plate.

12. An end effector for a surgical forceps, the end effector comprising:
- a sealing plate disposed on a first jaw member and defining an opening therethrough;
- an overmold tooth extending through the opening and beyond the sealing plate towards a second jaw member; and
- a hard stop extending beyond the sealing plate towards the second jaw member further than the overmold tooth, the hard stop configured to control a gap distance between the first and second jaw members.

13. The end effector according to claim 12, wherein the hard stop is disposed adjacent to an end of the sealing plate.

14. The end effector according to claim 12, wherein the sealing plate includes a longitudinally extending blade slot defined therein.

15. The end effector according to claim 12, further comprising:
- a support base disposed on the first jaw member; and
- an insulative material disposed on the first jaw member between the support base and the sealing plate.

16. The end effector according to claim 15, wherein the overmold tooth extends from the insulative material through the opening and beyond the sealing plate towards the second jaw member.

17. The end effector according to claim 15, further comprising an insulative housing mounted to the support base and encapsulating at least a portion of each of the support base, the insulative material, and the sealing plate.

* * * * *